(12) United States Patent
Hochgraeber et al.

(10) Patent No.: US 8,196,456 B2
(45) Date of Patent: Jun. 12, 2012

(54) AUTOSAMPLER FOR HIGH-PERFORMANCE LIQUID CHROMATOGRAPHY

(75) Inventors: Hermann Hochgraeber, Offenberg-Neuhausen (DE); Gervin Ruegenberg, München (DE)

(73) Assignee: Dionex Softron GmbH, Germering (DE)

( * ) Notice: Subject to any disclaimer, the term of this patent is extended or adjusted under 35 U.S.C. 154(b) by 733 days.

(21) Appl. No.: 12/331,228

(22) Filed: Dec. 9, 2008

(65) Prior Publication Data

US 2009/0145205 A1  Jun. 11, 2009

(30) Foreign Application Priority Data

Dec. 10, 2007  (DE) .................. 10 2007 059 651

(51) Int. Cl.
*G01N 30/84* (2006.01)
(52) U.S. Cl. ...................................... 73/61.55
(58) Field of Classification Search ............... 73/61.55, 73/863.01, 864.81–864.87; 137/625.46; 135/625.15, 625.46; 251/160
See application file for complete search history.

(56) References Cited

U.S. PATENT DOCUMENTS

| | | | |
|---|---|---|---|
| 3,530,721 A | 9/1970 | Hrdina | |
| 4,242,909 A | 1/1981 | Gundelfinger | |
| 4,939,943 A | 7/1990 | Strohmeier | |
| 5,010,921 A * | 4/1991 | Nohl | 137/625.46 |
| 5,654,201 A | 8/1997 | Capuano | |
| 6,155,123 A | 12/2000 | Bakalyar | |
| 6,382,035 B1 | 5/2002 | Nichols | |
| 6,453,946 B2 | 9/2002 | Nichols et al. | |
| 2009/0050212 A1 * | 2/2009 | Dourdeville et al. | 137/14 |

FOREIGN PATENT DOCUMENTS

| | | |
|---|---|---|
| EP | 0 409 522 A | 1/1991 |
| WO | WO 2006/021071 A | 3/2006 |
| WO | WO 2006/083776 A | 8/2006 |
| WO | WO 2006/083776 A2 | 8/2006 |
| WO | WO 2007/062642 A1 | 6/2007 |

OTHER PUBLICATIONS

Communication from German Patent and Trademark Office dated Oct. 27, 2008 (German Application No. 10 2007 059 651.2-41)(4 Pages).

* cited by examiner

*Primary Examiner* — Hezron E Williams
*Assistant Examiner* — Tamiko Bellamy
(74) *Attorney, Agent, or Firm* — The Culbertson Group, P.C.

(57) ABSTRACT

An autosampler for high-performance liquid chromatography (HPLC) with a high-pressure injection valve (1, 2) having improved life, particularly in high pressure operation. The geometry of the valve components and the connections of the high-pressure injection valve are provided such that the switching processes do not take place in a deleterious direction. The grooves in rotor (2) and/or the port opening cross sections (131, 151) in stator (1) and the rotational direction are selected such that fluid flows from grooves under high pressure in the direction of narrow, substantially pressure-free ports are avoided. This applies in particular to the switching process from INJECT to LOAD, since the sample loop contains a relatively large dead volume of compressed fluid. In addition, the valve can be controlled according to the invention in such a manner that an appropriate time is available for reducing harmful or undesired pressure differences.

20 Claims, 12 Drawing Sheets

AUTOSAMPLER FOR HIGH-PERFORMANCE LIQUID CHROMATOGRAPHY

FIELD OF THE INVENTION

The invention relates to an autosampler for high-performance liquid chromatography (HPLC), in particular an autosampler of the type used for injecting samples in HPLC.

BACKGROUND

A sample to be examined in HPLC must be fed into a high-pressure liquid stream, the latter being interrupted for as short a time as possible. High-pressure injection valves that allow a nearly interruption-free switching of the liquid stream are used for this purpose. Such a structure is described in U.S. Pat. No. 3,530,721, for example; the original application for the latter originates from the year 1965.

The refinement of such an injection valve is mentioned, for instance, in U.S. Pat. No. 4,242,909. The basic principle of the valve shown there has largely established itself since then in HPLC. Since the present invention is based on this type of valve, the principle will be described in detail below.

FIG. 1 shows such a high-pressure valve according to prior art in a schematic representation. It consists of a stator 1 and a rotor 2. The stator has a total of six input and output ports 11, 12, 13, 14, 15, 16. The injection valve can be connected via these ports to other functional elements of the HPLC system by means of capillary connections. For the sake of clarity, the necessary high-pressure threaded connectors are not shown in FIG. 1. The ports are formed inside the valve as bores leading to the other side 10 of stator 1. In practically realized valves, differing from the simplified representation in the drawing, the hole circle diameter on the side of the high-pressure connectors is usually larger than on the other side 10. The rotor has a number of arc-shaped grooves 21, 23, 25, which are aligned precisely with the bores of the input and output ports. This is indicated in FIG. 1 by dotted lines. For clearer representation, the rotor is drawn in FIG. 1 with a spacing from the stator. In the assembled state of the valve, this spacing is basically nil; therefore, the surface 20 of rotor 2 rests directly on the surface 10 of stator 1, as is shown in FIG. 2.

FIG. 2 shows the assembled valve from prior art ready for operation. The rotor is pressed against the stator with a pressure force that is indicated by the arrow F, so that a common contact surface is formed between rotor 2 and stator 1, where the two parts seal together. The pressure force F is dimensioned such the arrangement is still sealed even at the highest pressures to be expected.

In the switching position of the valve shown in FIG. 1 and FIG. 2, grooves 21, 23, 25 are oriented with respect to input and output ports 11-16 such that they produce three connections between adjacent input and output ports; specifically, port 11 is connected via groove 21 to port 16, port 13 to 12 and port 15 to 14. Due to the sealing effect at contact surface 301, liquid supplied via port 11, for example, can exit only at port 12.

To switch the valve to a second position, the rotor can be rotated 60 degrees relative to the stator so that the grooves now connect those ports that did not have a connection previously. The direction of rotation is indicated in FIG. 1 by an arrow on the rotor.

The switching is performed by a motorized drive that can rotate rotor 2 with respect to stator 1. The drive was omitted in the drawing for the sake of clarity.

FIG. 3 shows a high-pressure valve according to prior art in a second switching position. As in FIG. 1, rotor 2 is drawn with a spacing away from the stator in order to achieve better recognizability. In the operation-ready assembled state of the valve, on the other hand, the rotor is pressed onto the stator analogously to FIG. 2.

In this second switching position, the above-mentioned connections are interrupted; instead, port 11 is now connected via groove 21 to port 12, port 13 to port 14 and port 15 to port 16.

The advantage of such valves is that they can be used for very high pressures with a sufficient pressing force. In addition, the bores of ports 11, 12, 13, 14, 15, 16 are arranged such that the ends lie on a circle with a very small radius. The grooves 21, 23, 25 then likewise lie on a circle with a very small radius, so that the dead volumes of the valve can be kept very small. High-pressure injection valves with two switching positions and six ports are generally used in HPLC to feed sample liquid into a liquid stream under high pressure. A common method is the so-called "pulled loop" injection principle. This will be explained schematically and in a simplified manner with reference to FIG. 4 and FIG. 5.

FIG. 4 shows a high-pressure valve according to prior art in a plan view; therefore, stator 1 and rotor 2 are directly one behind the other. The stator is shown as being transparent, so that the position of grooves 21, 23, 25 in the rotor can be recognized. The valve is in a first switching position and the rotational direction of the rotor into a second switching position is indicated by an arrow. The components described below are connected to the valve via capillary tubes, which are shown as thick lines in FIG. 4.

A high-pressure pump 40 that can supply a constant flow rate under high pressure is now connected to port 15. In the switching position of the valve as drawn, this flow reaches port 14 through groove 25, and then reaches a chromatographic column 41. A sample needle 44, which barely dips into a sample container 43, is connected to port 12. Instead of being moved into sample container 43, sample needle 44 can be moved into a waste container to dispose of excess liquid. The waste container is not shown in the drawings since whether sample needle 44 is in the sample container or the waste container is irrelevant to the explanation of the invention. A syringe 42 for drawing sample liquid is connected to port 11. The two remaining ports 13, 16 are externally connected to one another via a sample loop 50. Sample fluid can thereby be drawn from sample container 43 into sample loop 50 with the aid of syringe 42. The switching position of the valve as drawn is referred to as the LOAD position, since the sample material is being loaded into the sample loop. The term "load" will be used for this in the remainder of the description. In order to feed the sample material into the high-pressure liquid stream, the valve is switched over to a second switching position, which is shown in FIG. 5.

FIG. 5 shows the high-pressure valve according to prior art in the same representation as in FIG. 4, but in its second switching position. A possible rotational direction of the rotor back into the first switching position is again indicated by an arrow. Now sample loop 50 is looped into the liquid path between pump 40 and column 41. The sample liquid previously drawn into sample loop 50 is thereby transported with the liquid stream coming from pump 40 into column 41, where the chromatographic separation takes place. Additional components for analysis, which are omitted from FIGS. 4 and 5 for the sake of clarity, are generally connected downstream of the column. The switching position of the valve as drawn is referred to as the INJECT position, since the sample material is being injected into the high-pressure liquid. The term "inject" will be used for this in the remainder of the description.

The injection principle as described is used on a standard basis in HPLC, sometimes in modified form. The basic mode of operation with LOAD and INJECT is always the same, with a great variety of implementations in use. For instance, U.S. Pat. No. 4,939,943 describes an autosampler in which a high-pressure syringe, which simultaneously is part of sample loop 50, is used in place of syringe 42. Sampling needle 44 is a component of the sample there as well. The valves that are used can also differ from the above-described design, e.g., additional ports for additional functions can be present; the arrangement of the grooves can also deviate from the plan shown in the drawings. The invention can be applied accordingly to such different designs of samplers as well.

As further prior art one can mention a special construction of high-pressure valves. Such valves are commercially available from Rheodyne LLC, California, e.g., models 7710 and 9710, and allow nearly interruption-free switching of the pump flow.

The basic principle of such valves from prior art corresponds very closely to FIGS. 1-5, and will be explained with reference to FIG. 4. In addition to the grooves 21, 23, 25 in rotor 2, there is also a single groove in stator 1 that, originating from port 14 in the stator, runs parallel to groove 25, but ends before reaching port 15.

During the switching process from the LOAD position to the INJECT position, the direct connection between ports 15 and 14 remains intact at first. The direct connection is not interrupted until just before groove 25 produces the connection between ports 15 and 16. The same effect can also be obtained by reversing the direction of rotation, with the groove originating from port 15 and ending even before reaching the bore of port 14. This function is referred to by the manufacturer as "make-before-break," since the existing connection is not interrupted until the new connection is produced.

A similar injection high-pressure valve and an autosampler for HPLC that is realized with it is also described in WO 2006/083776 A2. This publication is concerned with the avoidance of pressure variations that are produced by samplers or switching processes in the high-pressure valves, affect the chromatography column, and can damage or destroy it. As a solution, a high-pressure injection valve is specified that, in addition to the grooves provided in the rotor, has at least one extra groove in the stator that serves to maintain the connection of the two high-pressure ports to which the pump and the column are connected for as long as possible during the switching from LOAD to INJECT. The connection is even maintained when the groove permanently connected to one of the sample loop ports reaches the pump port, so that the initially pressure-free sample loop is simultaneously subjected to the pump pressure. Then the high-pressure ports are cut off, only in the last angle range of the rotor's rotational movement, and the column port is connected to the respective other sample loop port. In this manner, almost no pressure change in the column is generated. The column is nearly always subjected to the pump pressure. It is indicated in this document that when there is a shift from INJECT to LOAD, the sample loop can be depressurized in an optimal manner, by means of a corresponding lengthening of the groove in the rotor or by providing a stator groove formed in the stator, by connecting the port connected to the syringe to the rotor groove being moved towards it, and thus to the respective sample loop port, before the other sample loop port is connected to the port connected to the sample needle. While it is possible to achieve a defined decompression of the sample loop due to this advancement, the critical switching states described below, in which a fluid flow into a narrow port can lead to damage to the rotor and/or the stator, arise here as well. In recent years, a trend toward separating columns with a small particle size has been observed in HPLC. Such separating columns allow better separation performance and a faster separation, which is why this is referred to as fast HPLC.

Since the flow resistance increases strongly with decreasing particle size, considerably higher pressures are required for fast HPLC. The maximum column pressure that appears is typically between 100 and 400 bar in conventional HPLC, while 600-700 bar are required for fast HPLC, sometimes even more than 1000 bar. A trend is already beginning to emerge in the direction of columns with even better separation power, which require even higher pressures of up to ca. 2000 bar.

In order to be able to operate high-pressure injection valves at such high pressures, the pressure force F (see FIG. 2) must be correspondingly increased for the valve to maintain integrity. In order for the rotor, which is normally fabricated from plastic for technical and cost reasons, to withstand this force, glass-reinforced or carbon fiber-reinforced plastics are used according to prior art. In addition, there is an increased material stress due to the higher pressure force F and consequently there is excessive wear, so that the service life of the valve (number of switch operations) is unsatisfactory.

This problem can be solved by appropriate material selection or coating. Thus, U.S. Pat. No. 6,453,946 describes a special coating that allows a cost-effective production of rotor and stator and simultaneously sharply reduces the wear on the materials.

It has been shown that such improved valves do behave more favorably, but fail during operation at very high pressures after a relatively small number of switching cycles.

More detailed study of such failed valves from prior art has shown that the failures mainly occur due to material erosion at certain points of the rotor. FIG. 6 shows a photo of such a damaged rotor. Grooves 21, 23, 25 appear shaded due to the side-lighting. The damaged areas 201, 202 are marked by circles and lie in the extension of grooves 23 and 25. In the case of the damage at 201, a deep hole was created in the rotor.

It was additionally found that damage appeared on the stator as well, more particularly, in the vicinity of the bores for the ports. FIG. 7 shows the photo of a such a damaged stator with damaged areas 101, 102.

The origin of such damage can be explained as follows.

In the INJECT position of FIG. 5, sample loop 50 and grooves 23 and 25 are under high pressure. During the changeover process to the LOAD position (FIG. 4), groove 23 remains under high pressure since the sample loop maintains the pressure due to the compressibility of the solvent contained in it. FIG. 8 shows the position of groove 23 in side view, shortly before the end of the changeover from INJECT to LOAD, when the damage in the rotor appears. The curvature of groove 23 is not taken into account in the drawing. Only the area of rotor 2 around groove 23, and only the area of stator 1 around ports 12 and 13, are shown.

The transition from the bores of ports 12, 13 to the sealing surface has, as do all ports 11-16, a respective bevel 121, 131. Sharp edges or burrs that could damage the rotor are thereby avoided. In the position shown in FIG. 8, groove 23 has just reached bevel 121, so that a very small passage has formed between the end of the groove and port 12.

Sample loop 50, and therefore groove 23 as well, are still under almost full pressure, whereas port 12 is connected to sample container 43 or the waste container and therefore has normal air pressure. Thus, the entire pressure difference acts on the very small passage, which simultaneously has only a very short length.

As in a nozzle, this "bottleneck" leads to extraordinarily high flow speeds, and the energy stored in the sample loop due to the compressibility of the solvent is converted into kinetic energy. As in the case of water-jet cutting, a very high energy density arises, which can damage the material in the vicinity.

In FIG. 8, the solvent flowing in from the sample loop is designated by an arrow 61, the solvent flowing out in the direction of the sample container or waste container is designated by an arrow 62, and the flow pattern on bevel 121 is designated by a bundle of arrows 63. The flow that overcomes the bottleneck on the bevel strikes the opposite edge of the bevel at extremely high speed and is deflected there, so that a small amount at this point is virtually washed out. This process is repeated with each switching cycle, so that the damage accumulates, which can lead to the hole 201 shown in FIG. 6.

FIG. 9 shows the flow pattern 63 as in FIG. 8, but in a perpendicular view from above. It is recognizable in this representation that, in striking the opposite edge of bevel 121, the flow 63 is, in a manner, focused by the curved shape onto the damage point, which further amplifies the deleterious effect.

The effect shown in FIG. 8 likewise appears in the switch back from LOAD to INJECT when groove 25 reaches port 16. At this moment, sample loop 50 is depressurized, since it is connected to sample container 43 in the LOAD position. Groove 25, on the other hand, is under the full pressure of the pump. This leads to the damage 202 at the end of groove 25 as shown in FIG. 6. The individual damage patterns differ from one another to some extent, since the associated components (e.g., flow resistance, stored fluidic energy) have an influence.

As is recognizable in FIG. 6, the problem does not appear at the other ends of the grooves, although the same pressure differences between the respective ports are in effect there to some extent. In the changeover from INJECT to LOAD, for instance, depressurized groove 21 reaches port 16, which is connected to sample loop 50, which is under pressure. Nonetheless, no damage occurs at the end of groove 21.

This can be explained with reference to FIG. 10 as follows.

FIG. 10 shows, in the same representation as FIG. 8, the situation shortly before the 11 LOAD position is reached, i.e., before groove 21 reaches port 16. Here the flow 64 enters via port 16, then flows through the bottleneck past bevel 161 into groove 21 and again exits as a flow 65 at port 11. Here too there is a bottleneck at the transition from port 16 to groove 21, at which a high pressure difference is in effect and thus extremely high flow velocities occur. The essential difference from FIG. 8 is that the flow 66 flows through this bottleneck in the opposite direction from the flow 63. The flow thus does not strike the opposite edge of bevel 161 nor any other solid material, but only the fluid present in groove 21. Therefore the flow is braked, or the kinetic energy is reduced, to such an extent that the remaining kinetic energy is too small to cause material damage.

Thus it can be assumed that under otherwise equal conditions a switching process with a reverse flow direction is not harmful. This recognition is used, as described below, for the solution of the problem according to the invention.

In the situation shown in FIG. 10, i.e., the reaching of the LOAD position, however, there is an undesired pressure surge on the syringe 42 connected to port 11 (FIG. 4), since the pressure in sample loop 50 discharges via port 11 at this moment.

The switching directions of the valve shown in FIGS. 4 and 5 are not mandatorily specified according to prior art, instead the switching from the LOAD to the INJECT position can also be done in the opposite rotational direction of the rotor. In this case the damage is avoided at the above-mentioned positions, but identical damage appears at different positions. This can be explained analogously to the consideration above.

The previous discussions explained the damage appearing in rotor 2, but not the damage in stator 1 shown in FIG. 7. This can be explained as follows.

The rotors 2 consist of fiber-reinforced plastics, as already explained. In the manufacturing of grooves 21, 23, 25, it is not possible to completely prevent the ends of the fibers from protruding from the plastic. Such protruding fibers are also found particularly in the vicinity of the edges of the grooves, i.e., in the direct vicinity of the surface of stator 1 in the assembled state of the valve. If, as shown in FIG. 8, the solvent flows from groove 23 to port 12, then the protruding ends of the fibers at the left upper edge of groove 23 are situated precisely where the flow 63 passes through the bottleneck at extremely high speed. The ends of the fibers are thereby pressed into the bottleneck and cause abrasive damage there, particularly because rotor 2 is pressed against stator 1 during the switching of the valve.

This damage also does not occur if the flow direction is reversed as in FIG. 10. In this case, the ends of the protruding fibers are oriented to the right by the flow 66, i.e. in the direction of the center of groove 21, where they cannot cause damage due to abrasion.

For this reason, the damage 101, 102 shown in FIG. 7 occurs at the same ports at which the damage 201, 202 shown in FIG. 6 appears, namely ports 12 and 16.

The damage mechanism as described is only effective if the situation illustrated in FIG. 8 occurs at one of the involved ports. This is the case for only a moment during the switching processes from LOAD to INJECT and vice versa. Therefore, an improvement can be achieved by accelerating this switching process. In this manner, the duration of the critical situation can be shortened and thus the damage can be reduced. Of course, the damage cannot be completely avoided in this manner, but only reduced by precisely the extent to which the switching speed is increased. The leeway for an even higher switching speed is only slight, however, since this would greatly increase the effort and therefore the costs.

Another approach to a solution could be to change the shape of the bevels 121, 131, in particular, to enlarge them so that the flow is directed onto the rotor with less intensity. Here as well, there is only a slight leeway since the bevels in valves according to prior art are optimized such that as little abrasion as possible occurs due to the switching process and the dead volumes are as small as possible. Furthermore, it is at best possible to avoid the damage 201, 202 in the rotor by means of such an approach, but not the damage 101, 102 in the stator.

SUMMARY OF THE INVENTION

The present invention provides an autosampler for HPLC in which the required switching of liquid streams between very high pressure differences is possible by means of a high-pressure injection valve, with a sufficient service life of the high-pressure injection valve being simultaneously guaranteed. The autosampler and, in particular, the high-pressure injection valve it comprises should additionally have an easily realized structure. Additional dead volumes should be avoided as much as possible.

In the prior art, the high-pressure injection valves are damaged at least in part by an unsuitable selection of the switching direction, i.e., the direction of the rotational movement of the rotor, when very high pressure differences are to be switched. Such damage can be avoided if the geometry of the valve components is adapted in a simple manner and if the connection of the valves is set up such that the switching processes do not take place in a harmful direction. According to the invention, damage to the valves during shifting from INJECT to LOAD is avoided, in particular, by providing and constructing at least three grooves and/or the port opening cross sections in such a manner, and selecting the rotational direction in such a manner that, in a rotation of the rotor from the INJECT position into the LOAD position, the sample loop under high pressure is decompressed in such a manner (a) that the grooves and/or the port opening cross sections are constructed and arranged such that the connection between the sample loop port and the load port due to the movement of the groove permanently connected to the respective load port in the direction towards the respective sample loop port is produced and maintained before the connection between the other sample loop port and the other load port is produced and maintained such that results due to the movement of the groove permanently connected to the respective sample loop port in the direction of the respective load port (advancement function for decompressing the sample loop), or (b) that an additional tension-relieving groove (66) is provided in rotor (2) that is constructed such that before reaching the LOAD position, in a defined rotational position or over a defined angular range, a connection is produced and maintained between the sample loop port (13) and the load port (11) that are not permanently connected to a groove, wherein the end of the tension-relieving groove (66) that is connected to the sample loop port 13 and/or the port opening cross sections runs over a sufficiently long tension-relieving region concentrically and in the circumferential direction, which is dimensioned such that the flow speeds of the fluid flow that results at the achievement of the overlapping of the tension-relieving groove (66) and the port opening cross sections are reduced sufficiently that damage to stator (1) and/or rotor (2) is avoided.

The sample loop port that is first connected for defined decompression to the respective low-pressure side port is under high pressure so that a flow from the port in the direction into the respective groove or tension-relieving groove is produced in any case. In this manner, damage to the rotor and stator is avoided even at extremely high pressures.

It may be remarked at this point that theoretically the at least three grooves need not run circumferentially and concentrically to the rotational axis over the entire length. The grooves or the groove-shaped extensions of the port cross section openings must run circumferentially and concentrically to the rotational axis at least in the (narrow) angle ranges inside of which are situated the positions of stator and rotor relative to one another in which there is to be a fluid flow. With such a construction of the high-pressure injection valve there no longer exist any grooves that are permanently connected to a port. Even with such designs, however, the advantage is achieved that high pressure differences are switched only in such a manner that a fluid flow from a port under high pressure or a groove-shaped port opening cross section arises only into an approximately pressure-free groove that runs in a circumferential direction at least in a sufficiently long tension-relieving range.

To that extent, references in this document to grooves extending in the circumferential direction and concentrically to the axis of rotation are to be understood to mean that they also include those embodiments in which this condition is fulfilled only within applicable ranges. The same applies to references to ports that are permanently connected to a groove during the switching. This also subsumes embodiments in which the ports in question are connected to the respective grooves only in crucial positions of stator and rotor.

According to one configuration of the invention, the groove that is moved towards the adjacent sample loop port (load port groove) during the switching from the INJECT position to the LOAD position, while maintaining the connection to the respective load port, can be constructed to lead the groove that is connected to the other sample loop port during the switching movement and connect it to the other load port in the LOAD position.

According to another configuration of the invention, the port opening cross section of the load port that is not permanently connected to a groove can extend in a groove shape in the direction towards that groove which is moved towards this sample loop port during switching from the INJECT position to the LOAD position while maintaining a connection to the respective load port, wherein the length of the groove-shaped extension of the port opening cross section is selected such that the function of advancement for decompressing the sample loop is realized.

This results in the advantage that no extension of the respective rotor groove is necessary, so that particularly in connection with a simultaneous lengthening of the adjacent rotor groove towards the rotor groove in question, as can be necessary to realize advantageous embodiments described below, no sealing problems due to closely adjacent groove ends can result.

According to an additional configuration of the invention, the groove that connects the two high-pressure ports in the LOAD position can be constructed to be sufficiently long such that the two high-pressure points are connected in the rotational position in which the decompression of the sample loop takes place, or over the entire angle range of the rotational movement in which the decompression of the sample loop takes place. The pressure drop in the column during the switching movement, particularly during the decompression process of the sample loop, is thereby minimized.

This advantage can also be achieved in an alternative embodiment of the invention in which the port opening cross section of the high-pressure port that is not permanently connected to a groove during the switching process is extended in a groove shape in the direction towards the groove which is moved towards this high-pressure port during the switching from the INJECT position to the LOAD position, while maintaining the connection to the respective load port, wherein the length of the groove-shaped extension of the port opening cross section is selected such that the two high-pressure ports (14, 15) are connected in the rotational position in which the decompression of the sample loop takes place, or over the entire angle range of the rotational movement in which the decompression of the sample loop takes place.

According to another configuration of the invention, the essentially pressure-free sample loop can be subjected to high-pressure during a rotation of the rotor from the LOAD position into the INJECT position in such a manner that the rotational direction is selected in such a manner, and the grooves and/or the port opening cross sections are constructed and arranged in such a manner (a) that first the connection is produced and maintained between one of the high-pressure ports and the sample loop port that is permanently connected to the groove during the switching movement, wherein the groove permanently connected to this sample loop port is moved for this purpose in the direction towards the pump port, and (b) that only subsequently is the connection between the other high-pressure port and the other sample loop port produced and maintained, wherein the groove permanently connected to the other high-pressure port during the switching movement is moved for this purpose in the direction towards the respective sample loop port (advancement function for pressurizing the sample loop).

It is thereby guaranteed that the application of pressure to the sample loop starts at the side on which the pump generates a fluid stream from a port subjected to pressure in the direction of an initially pressure-free port. After the sample loop has been placed under pressure, the groove still under the column pressure can be connected to the other sample loop port without the danger of damage to the rotor or stator, since the pressure difference is relatively small due to the short switching time, inside of which the column pressure falls only slightly.

This advancement of the connection of the pump port to the respective end of the sample loop with respect to the connection of the other end of the sample loop to the column port can be produced in that the groove (sample loop port groove) that is moved towards the adjacent high-pressure port during the switching from the LOAD position to the INJECT position, while maintaining the connection between the respective sample loop port and the adjacent high-pressure port, is constructed to be advanced with respect to the groove that is connected to the other high-pressure port during the switching movement and connects it in the INJECT position to the other sample loop port.

According to another configuration of the invention, the high-pressure injection valve can be constructed such that the port opening cross section of the high-pressure port that is not permanently connected to a groove during the switching process can extend in a groove shape in the direction towards the groove that is moved towards this high-pressure port while maintaining a connection to the respective load port during switching from the LOAD position to the INJECT position, wherein the length of the groove-shaped extension of the port opening cross section is selected such that the advancement function for pressurizing the sample loop is realized.

The advancement in this case, just as in the decompression of the sample loop, can also be generated by a combination of these measures, i.e., by an appropriate lengthening of the respective groove and simultaneously by a groove in the stator extending towards the groove in question from the respective port.

According to a preferred embodiment of the invention, the high-pressure injection valve has a controllable drive unit for the rotational movement of the rotor and a control unit. An automated autosampler can thereby be realized.

The control unit can control the drive unit such that the decompression of the sample loop during the switching from the INJECT position into the LOAD position takes place essentially completely via the predetermined sample loop port. For this purpose, the control unit can influence the speed of the rotational movement such that the time span over which a decompression of the sample loop can take place via the desired port is sufficient to guarantee an essentially complete decompression. For this purpose in particular, the control unit can slow the rotary movement over an angle range in which a decompression is possible, or can stop the rotary motion in this angle range for a predetermined time span.

In an analogous manner, the control unit can control the drive unit such that the pressurization of the sample loop during the switching from the LOAD position into the INJECT position takes place essentially completely via the predetermined sample loop port. For this purpose as well, the control unit can influence the speed of the rotational movement such that the time span over which a pressurization of the sample loop can take place via the desired port is sufficient in order to guarantee an essentially complete pressurization. For this purpose in particular, the control unit can slow the rotary movement over the angle range in which a pressurization is possible, or can stop the rotary motion in this angle range for a predetermined time span.

The described damage to the valves can thus be completely prevented according to the invention with minimal extra expenditure with respect to previously known samplers or valves. The service life of a high-pressure injection valve according to the invention is therefore limited only by the unavoidable abrasion between the rotor and the stator and possibly by the abrasive effect of particles such as contaminants or sample materials.

Additional embodiments follow from the subordinate claims, and the detailed description and drawings.

DETAILED DESCRIPTION OF PREFERRED EMBODIMENTS

Figure 2:
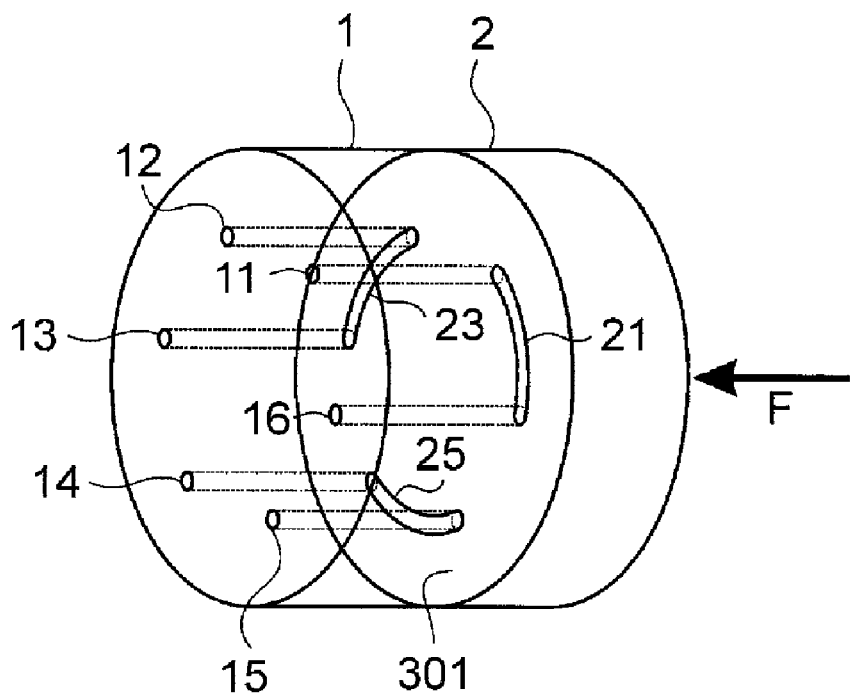
FIG. 2 shows the operation-ready installed high-pressure injection valve in FIG. 1 in a schematic perspective representation.
Figure 3:
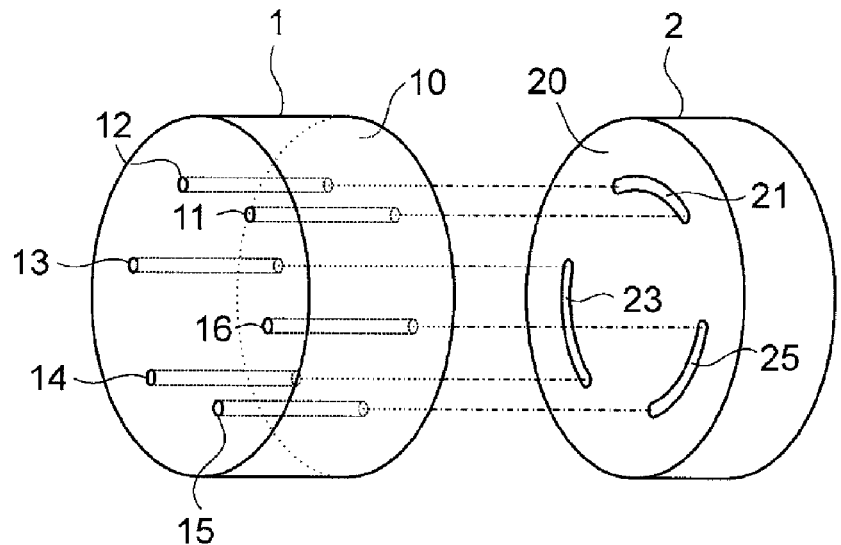
FIG. 3 shows a schematic perspective exploded view of the high-pressure injection valve in FIGS. 1 and 2 in a second switching position.
Figure 4:
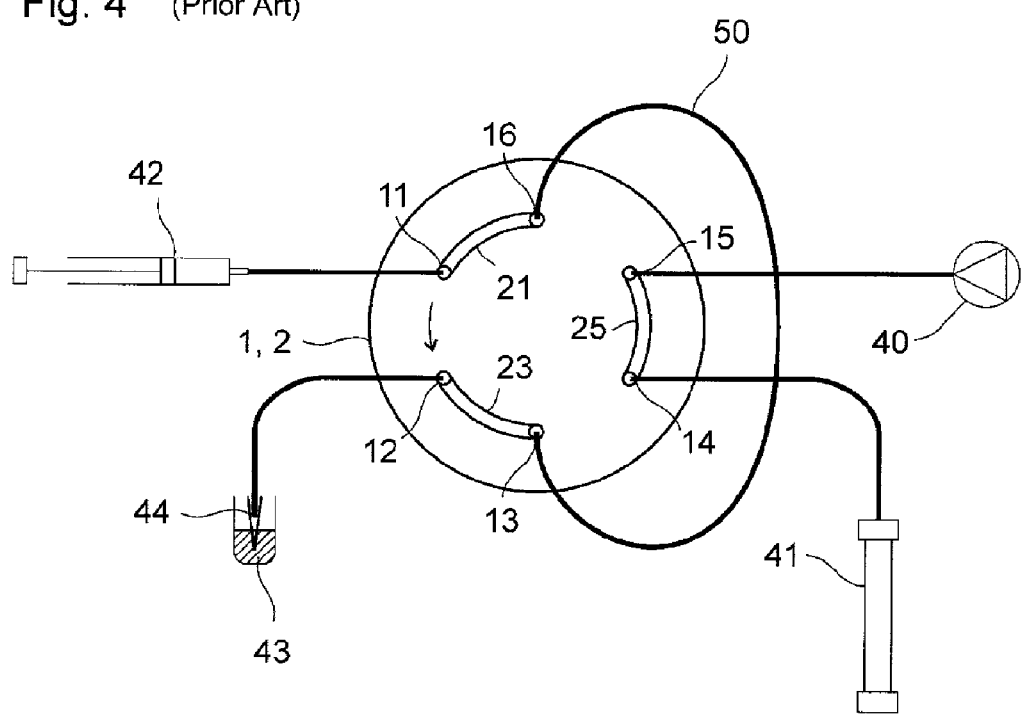
FIG. 4 shows a simplified schematic representation of an autosampler according to prior art with a high-pressure injection valve as in FIGS. 1-3 that is shown as a section in the area of the contact plane of the rotor and the stator, with connected fluidic components, wherein the valve is in the LOAD position.
Figure 5:
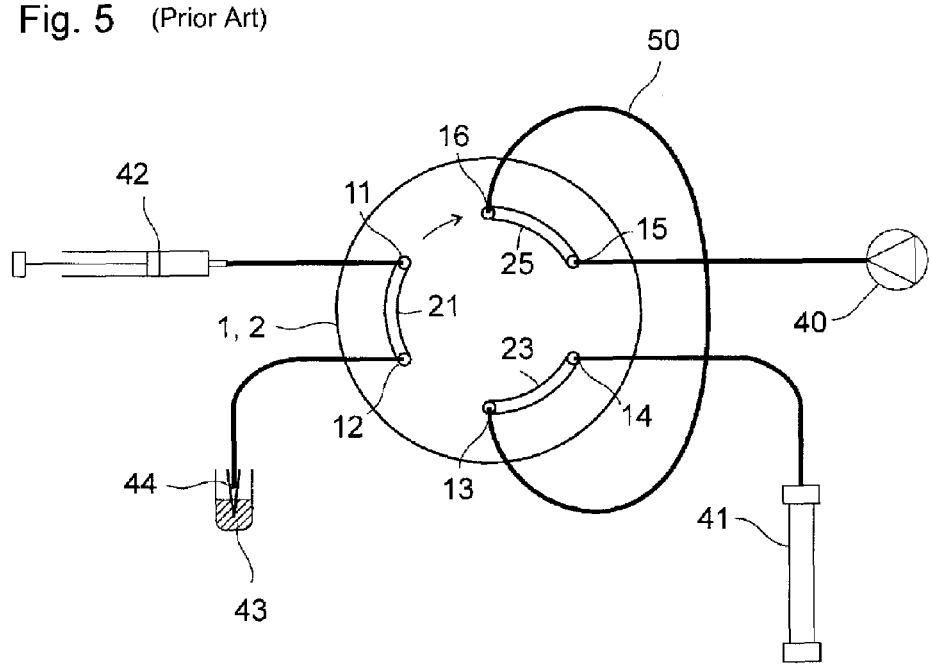
FIG. 5 shows a representation analogous to FIG. 4, but with the high-pressure valve in the INJECT position.
Figure 11:
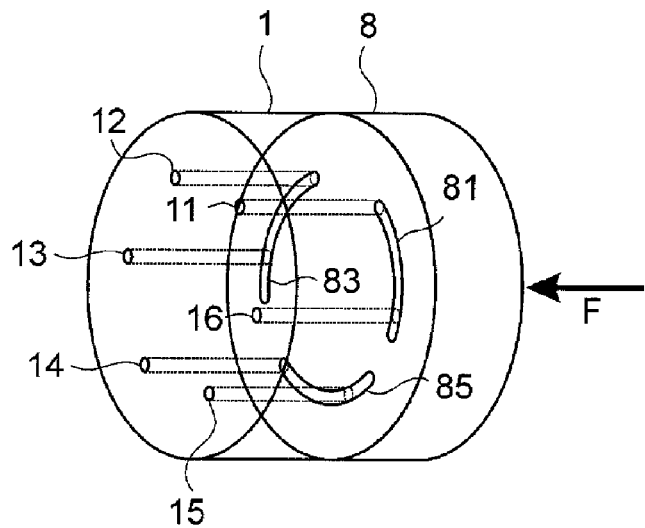
FIG. 11 shows a first embodiment of a high-pressure injection valve according to the invention in the operation-ready assembled state, in a schematic perspective view.
Figure 12:
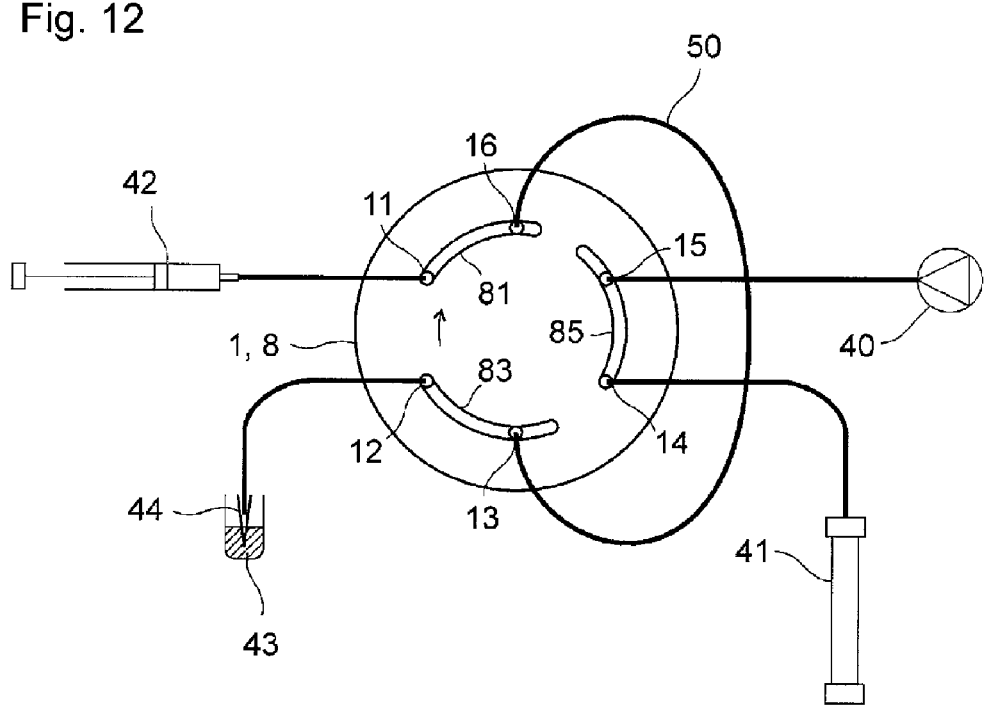
FIG. 12 shows a simplified schematic representation of a first embodiment of an autosampler according to the invention with a high-pressure injection valve as in FIG. 11 that is shown in section in the area of the contact plane of the rotor and the stator, with connected components, wherein the valve is in the LOAD position.

FIG. 11 shows a first preferred embodiment of a high-pressure injection valve according to the invention in a first switching position. The improved rotor 8 has grooves 81, 83, 85. The difference from the valve according to prior art (FIG. 2) is that grooves 83 and 85 were lengthened in comparison to grooves 23 and 25, so that they do not end at ports 13 and 15, respectively, in the first switching position but extend beyond them. Groove 81 was likewise lengthened in the other direction, so that it extends beyond port 16. Stator 1 is unchanged with respect to the prior art. This first embodiment is shown in a plan view in FIG. 12 and with connected external components. The representation, as well as the connections and mode of operation correspond exactly to FIG. 4, i.e., the valve is in the LOAD position. The extensions of grooves 83, 85 represent dead ends, which have no influence on the mode of operation in the LOAD position.

After the sample loop 50 has been filled, the valve is moved into the INJECT position. The switching direction is not arbitrary, unlike the prior art; according to the invention, the rotor must be turned in the direction of the arrow in the switching from LOAD to INJECT, so that groove 81 is moved towards port 15.

Figure 13:
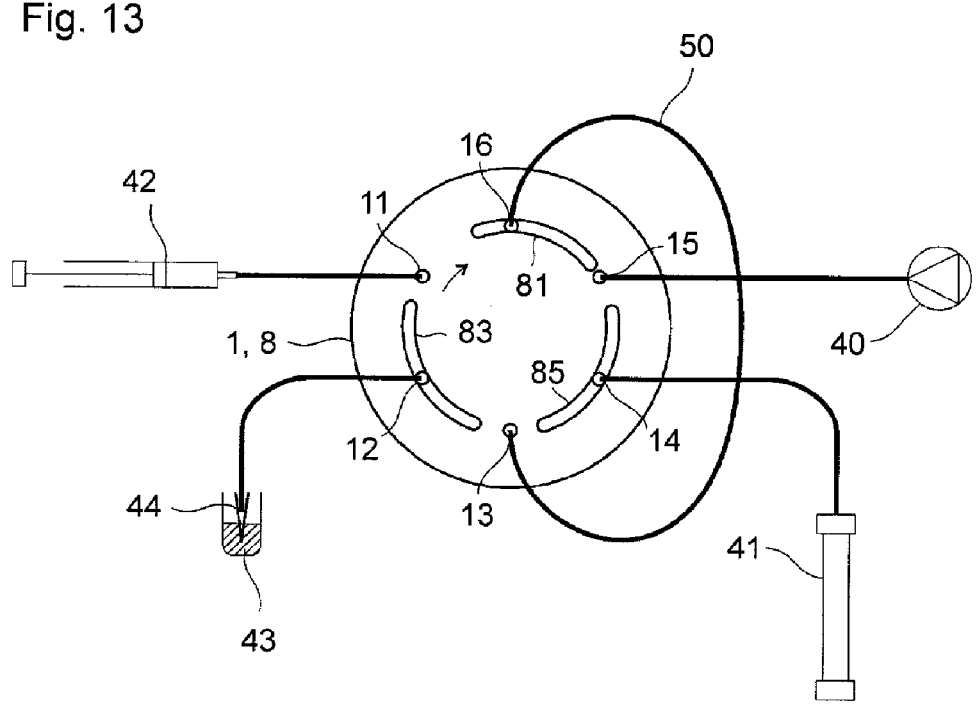
FIG. 13 shows the autosampler in FIG. 12, wherein the high-pressure injection valve is situated in the first critical phase during the switching from LOAD to INJECT

FIG. 13 shows the valve according to the invention in a first critical phase shortly before reaching the INJECT position. Ports 11 and 12 are both depressurized, so that no problems are expected there.

Figure 10:
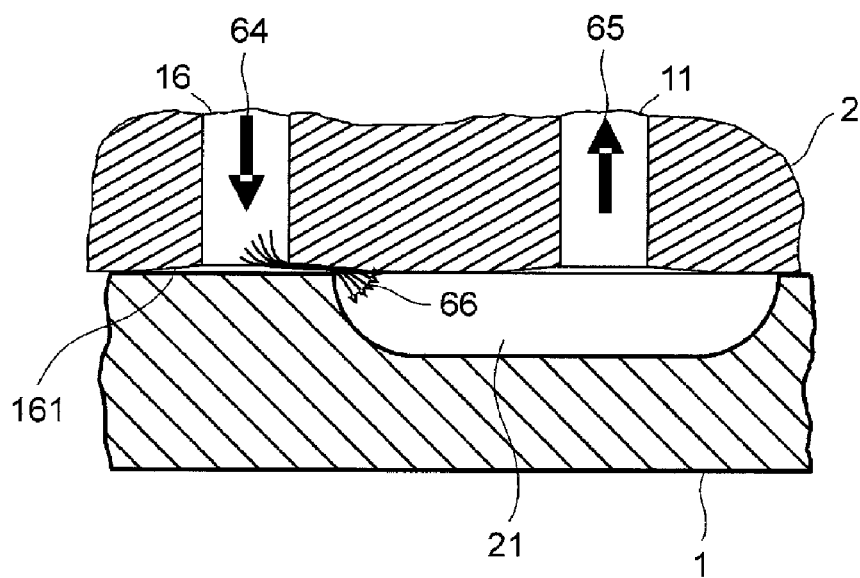
FIG. 10 shows a representation similar to FIG. 8, but with reversed flow direction of the fluid.

Groove 81 just reaches port 15, at which the pressure built up by the pump is present. The solvent flows from port 15 in the direction of groove 81. Thus, the flow relationships are analogous to FIG. 10 and there is no damage to rotor 8 or stator 1. The pump pressure can now put sample loop 50 under pressure via groove 81. During the process, the rotor turns further in the direction of the arrow.

Figure 14:
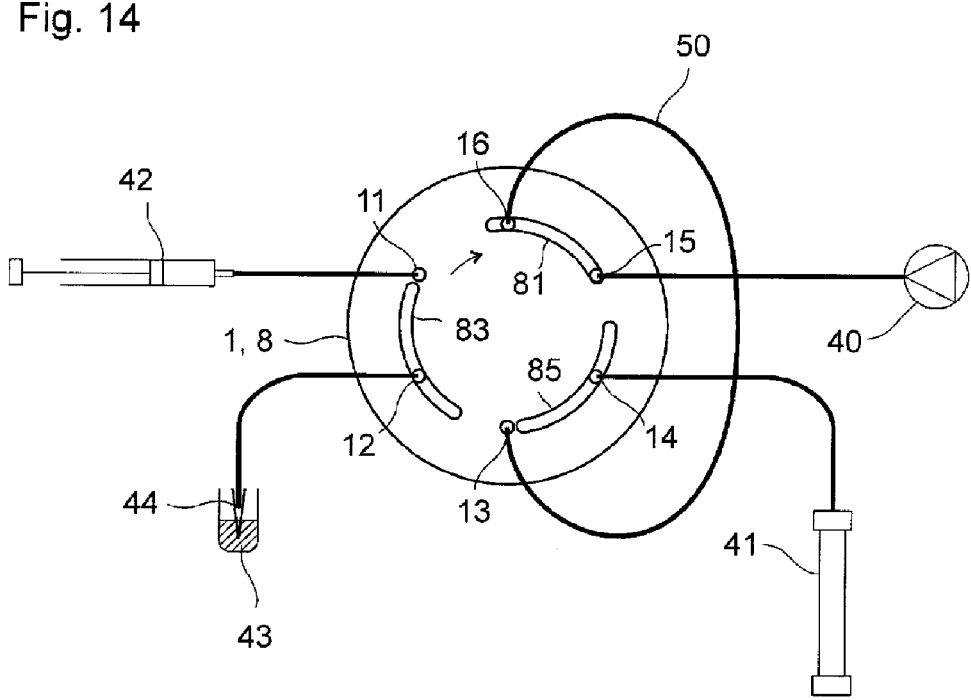
FIG. 14 shows the autosampler in FIG. 12, wherein the high-pressure injection valve is situated in a second critical phase during the switching from LOAD to INJECT.

FIG. 14 shows the valve according to the invention in a first critical phase shortly before reaching the INJECT position. In comparison with FIG. 13, the rotor has now turned sufficiently further that groove 85 is just reaching port 13. At this point, groove 81 already covers port 15 completely, so that sample loop 50 is subject to the full pressure of pump 40. Since pump 40 builds up pressure during the switching process, while the pressure in column 41 becomes lower, the flow direction here is analogous to FIG. 10 as well, i.e., from sample loop 50 via port 13 into groove 85. Therefore no material damage occurs here.

Figure 15:
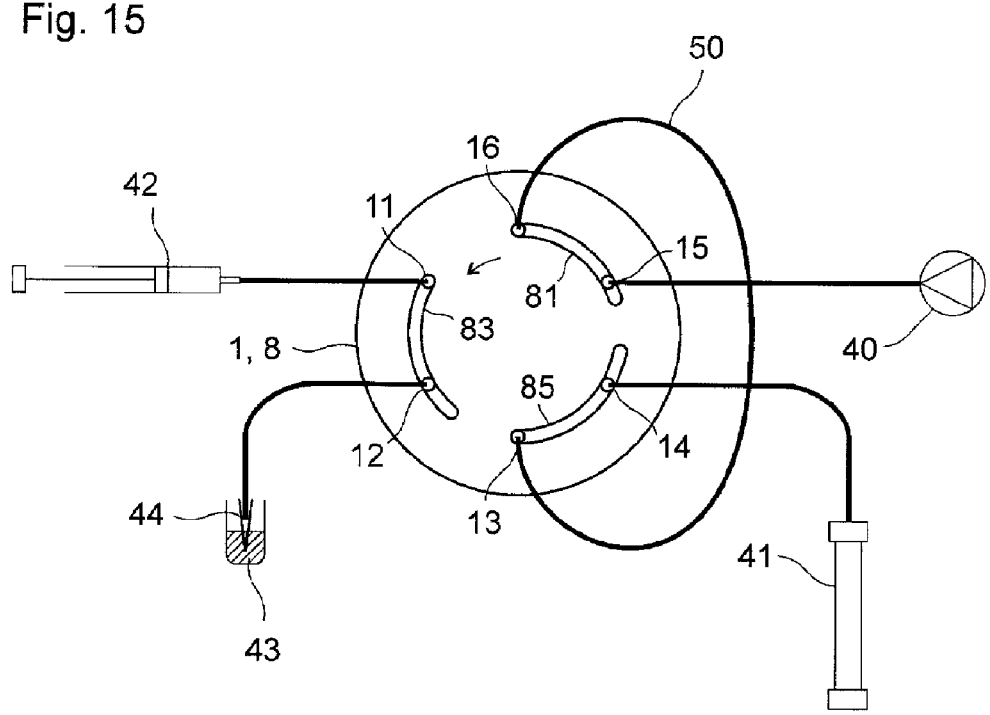
FIG. 15 shows the autosampler in FIG. 12, wherein the high-pressure injection valve is in the INJECT position.

FIG. 15 shows the valve according to the invention after it has reached the INJECT position. The flows run just as in a valve according to prior art; the sample material present in sample loop 50 is transported with the liquid stream of pump 40 into column 41.

The processes during the switching back of the valve into the LOAD position according to the invention must now be considered. This takes place in the reverse direction, as is indicated by an arrow in FIG. 15. Again only those switching processes in which large pressure differences appear are relevant.

Figure 16:
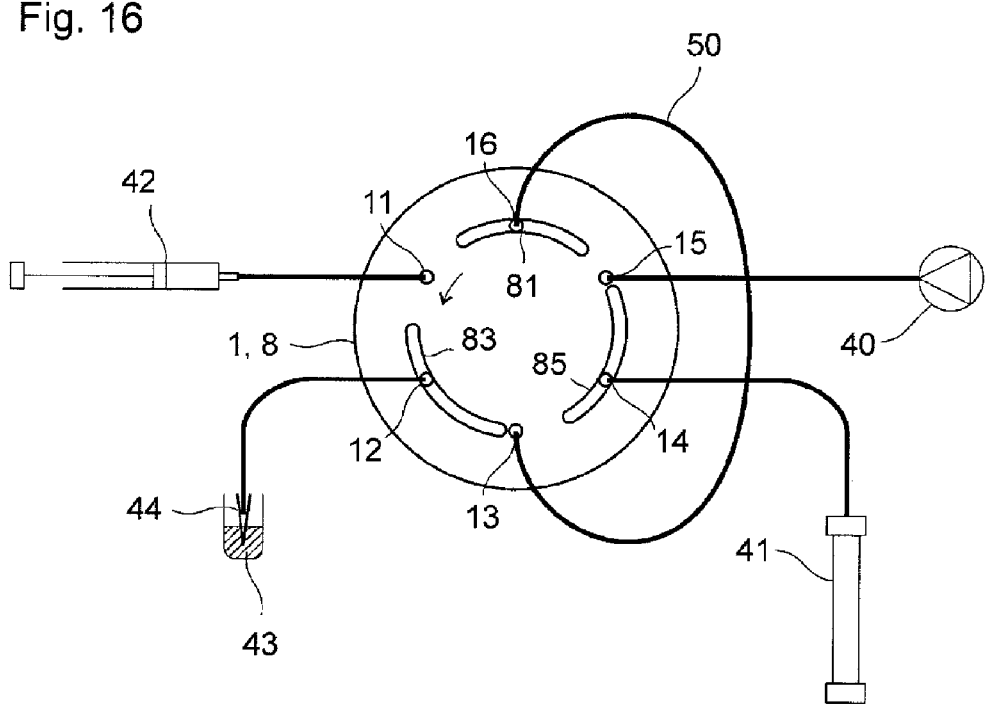
FIG. 16 shows the autosampler in FIG. 12, wherein the high-pressure injection valve is situated in a third critical phase during the switching from INJECT to LOAD.

FIG. 16 shows the third critical phase, which appears during the switch back from INJECT to LOAD. Groove 83, which is connected to pressure-free sample needle 44, reaches port 13, which is under the pressure of sample loop 50. In this case as well, the pressure reduction takes place analogously to FIG. 10, from port 13 to groove 83, so that no material damage occurs. The pressure of pump 40 can likewise be reduced from port 15 in the direction of groove 85, without damage occurring.

Figure 17:
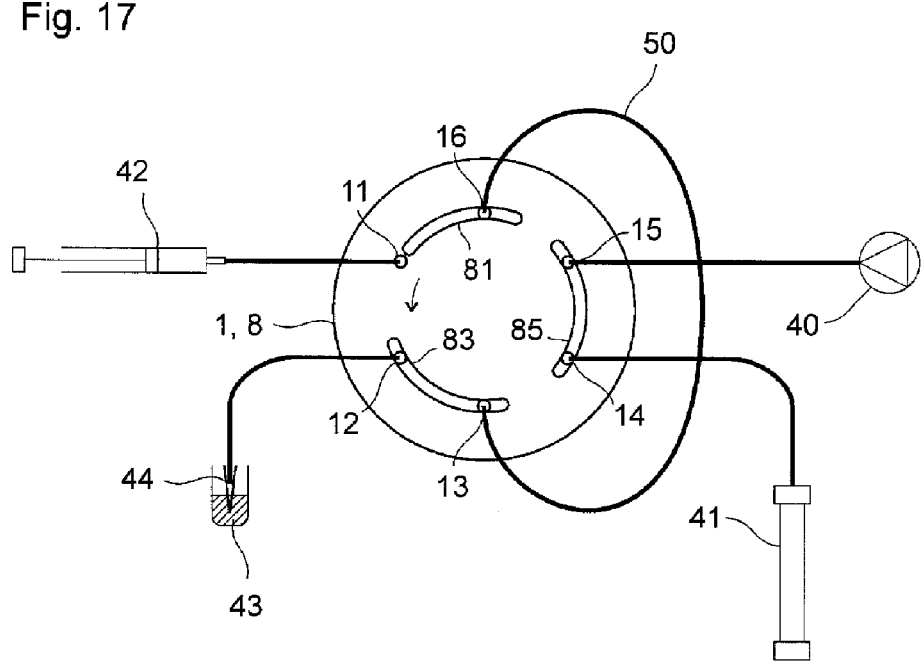
FIG. 17 shows the autosampler in FIG. 12, wherein the high-pressure injection valve is situated in a fourth critical phase during the switching from INJECT to LOAD.

FIG. 17 shows the position of the rotor shortly before reaching the LOAD position. At this point, port 13 is already completely covered by groove 83, so that the pressure in sample loop 50 can be quickly reduced. Therefore, no pressure difference is in effect between port 11 and groove 81, so that no harmful flow can form. As compared with the prior art this simultaneously has the advantage that no pressure surge appears at peak 42.

Figure 6:
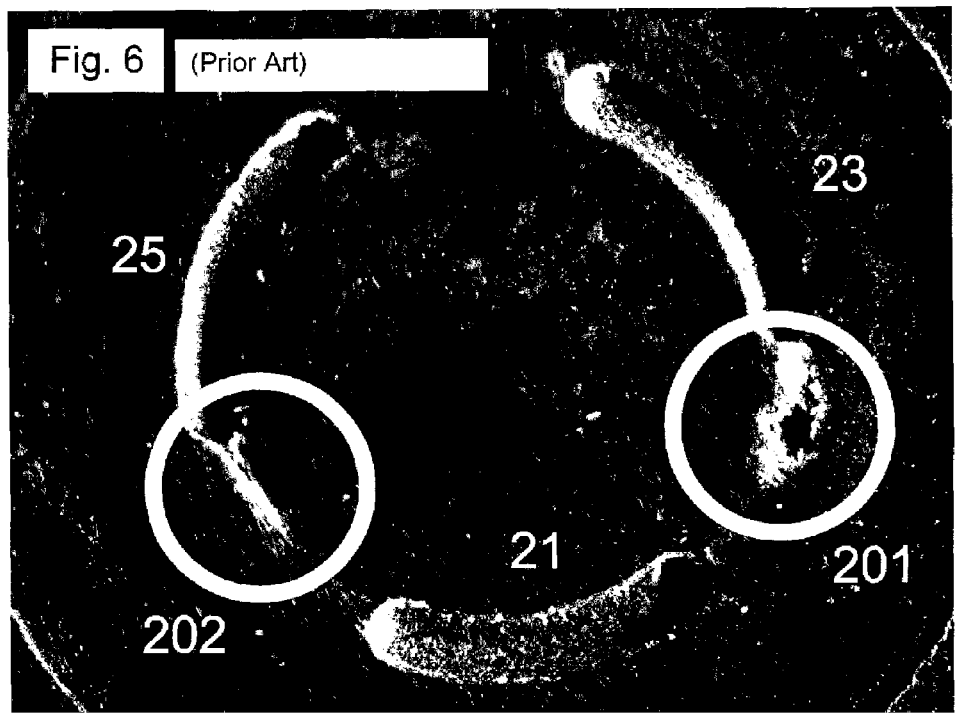
FIG. 6 shows a photo showing damage in the end face of the rotor of a high-pressure injection valve according to FIGS. 1-5 that was operated over a relatively long period at pressures above 600 bar.
Figure 7:
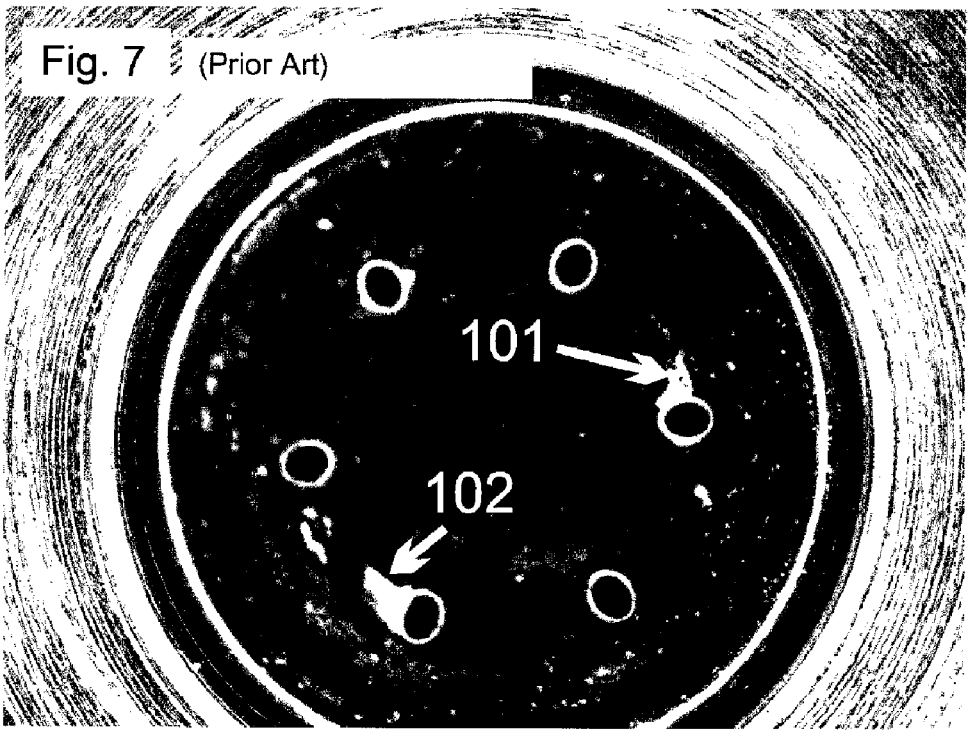
FIG. 7 shows a photo showing damage in the end face of the rotor of a high-pressure injection valve according to FIGS. 1-5 that was operated over a relatively long period at pressures above 600 bar.
Figure 8:
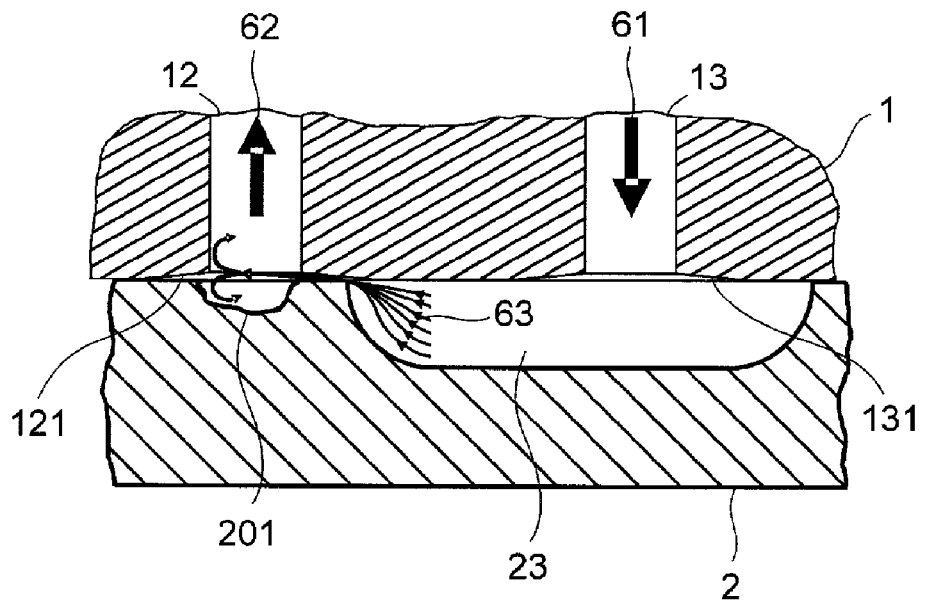
FIG. 8 shows a section parallel to the axis through the groove and two ports of the valve according to prior art in which the fluid flow that causes damage in the rotor is also shown.
Figure 9:
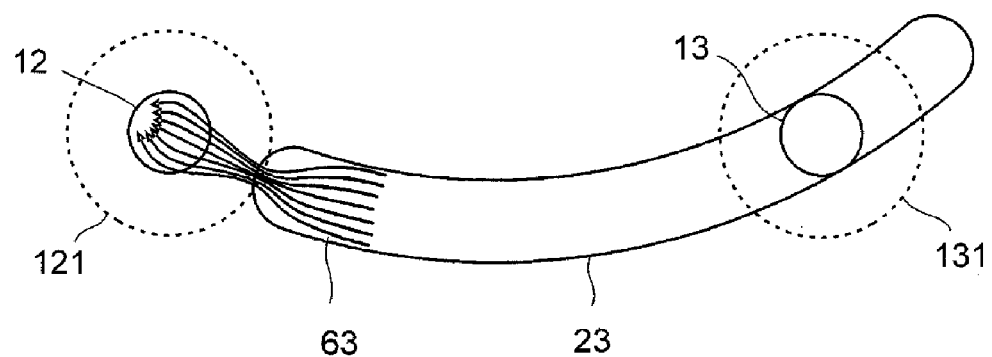
FIG. 9 shows a schematic representation of the groove and the two ports of the representation in FIG. 8 in a plan view in which the flow causing damage in the rotor is likewise shown.

The reaching of the LOAD position again corresponds to FIG. 12. This consideration shows that with the valve according to the invention, and while maintaining the switching direction specified by the invention, all switching processes in which high pressure differences appear run such that the pressure from the respective port is reduced in the direction of the groove. In this way, the damage to the rotor and stator shown in FIGS. 6 and 7 is avoided. In the first embodiment described to this point, the invention has, in principle, already solved the problem completely.

The mode of operation of the invention is based, among other things, on an expedient temporal sequence of the individual sub-steps of the switching processes. Due to the above-described lengthening of the grooves, the temporal sequence of the switching processes is established in such a manner that the damaging situations are avoided. The prerequisite for the mode of operation is that a sufficient pressure equalization can actually take place in the time between the individual sub-steps. Therefore, dynamic aspects must also be taken into account. In the changeover from the INJECT into the LOAD position, the pressure reduction begins in sample loop 50 as soon as the switching position of the valve shown in FIG. 16 has been reached. How quickly the pressure is reduced depends on the volumes and flow resistances of sample loop 50, groove 83, ports 12, 13, sample needle 44 and their connection capillaries. The moment of inertia and the compressibility of the liquid in these components also play a role. In addition, turbulent flows can appear due to the high flow velocities. For these reasons, the pressure reduction is a complex dynamic process that can last longer than expected under certain circumstances, particularly when a sample loop 50 with a large internal volume is used.

The time available for the pressure reduction should therefore be as long as possible. For this purpose, the groove 83 could be made as long as possible, so that it reaches port 13 in FIG. 16 earlier.

With increasing length of the grooves 81, 83, 85, however, the distance or width of the remaining ridge between the ends of the grooves, which is necessary for the sealing action of the valve, is reduced. Therefore the grooves must not be overly lengthened. A practical compromise is a lengthening of the grooves by roughly 5% to 35% relative to the original length of grooves 21, 23, 25. Since only the order of the switching processes is decisive for the functioning of the invention, the percentage by which the grooves are lengthened plays only a subordinate role.

The time available for the pressure equalization also depends on the rotational speed of rotor 8 during the switching process, in addition to the length of grooves 81, 83, 85. Since the flow paths are temporarily interrupted during the switching process, the drive unit of such valves according to prior art is designed such that the switching process runs as quickly as possible. For commercially available valves at this time, the total duration of a switching process lies in the range of tenths of a second, e.g., 0.2 s. Thus, the time available for pressure equalization in case of a lengthening of the grooves by 20%, for example, is on the order of ten milliseconds. In this time, pressure differences can generally be reduced to an extent that damage to the valve can no longer occur.

As already mentioned, a pressure surge onto syringe 42 can occur during the switching from INJECT to LOAD if the pressure in sample loop 50 is not reduced quickly enough. To avoid this, as complete a pressure equalization as possible should be achieved. In addition, a sudden pressure reduction due to dynamic processes can result in the formation of gas or vacuum bubbles, which leads to a severe slowdown of the pressure reduction. For these reasons, it is desirable to make as much time as possible available for pressure reduction.

This can be assured in a practical refinement of the invention by sharply braking the driving of the valve or stopping it completely for a short time, as soon as sample loop 50 is connected to needle 44 and pump 40 to column 41.

Figure 18:
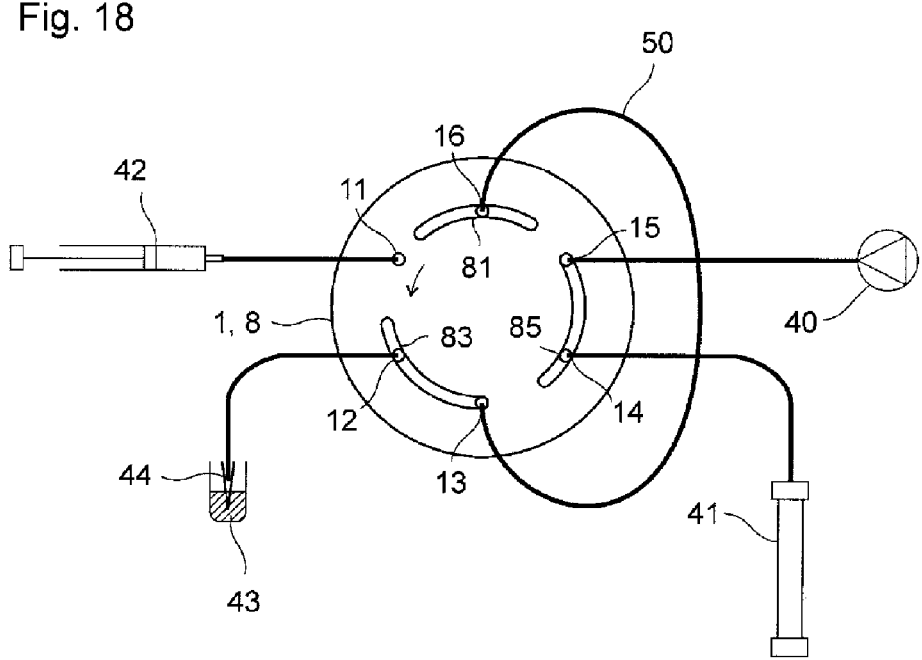
FIG. 18 shows the autosampler in FIG. 12 during the switching from INJECT to LOAD, wherein the high-pressure injection valve is in a position in which the sample groove is being decompressed.

FIG. 18 shows a possible position in which driving of the valve can be stopped or braked. This position is reached immediately following FIG. 16. Pump 40 is already connected via groove 85 to column 41, and sample loop 50 can reduce its pressure in the direction of sample needle 44 via groove 83. Since the next LOAD process need be carried out only much later, namely, after conclusion of the chromatographic separation process, sufficient time is now available for pressure reduction in sample loop 50. For this purpose, the valve driving can be stopped for a predetermined time after the position illustrated in FIG. 18 is reached, but before the position illustrated in FIG. 17 is reached. Operation after LOAD in FIG. 12 need continue only when sample loop 50 is to be filled again with new material.

Instead of completely stopping the driving of the valve, the speed of the drive unit can be markedly reduced after the position shown in FIG. 18 has been reached, so that rotor 8 runs only slowly to the LOAD position.

The achievement in both cases is that the pressure in the sample loop is reduced before the LOAD position is reached. Pressure surges onto syringe 42 can be completely avoided by this braking according to the invention.

In the discussions thus far, the injection has been performed in that a sample to be introduced into the high-pressure circuit is first drawn by syringe 42 into a fixed sample loop 50. This injection principle is referred to as "pulled loop" or "fixed loop." Additional widespread injection principles are the "pushed loop" and the "split loop." The invention can be applied 11 accordingly to these principles as follows.

Figure 19:
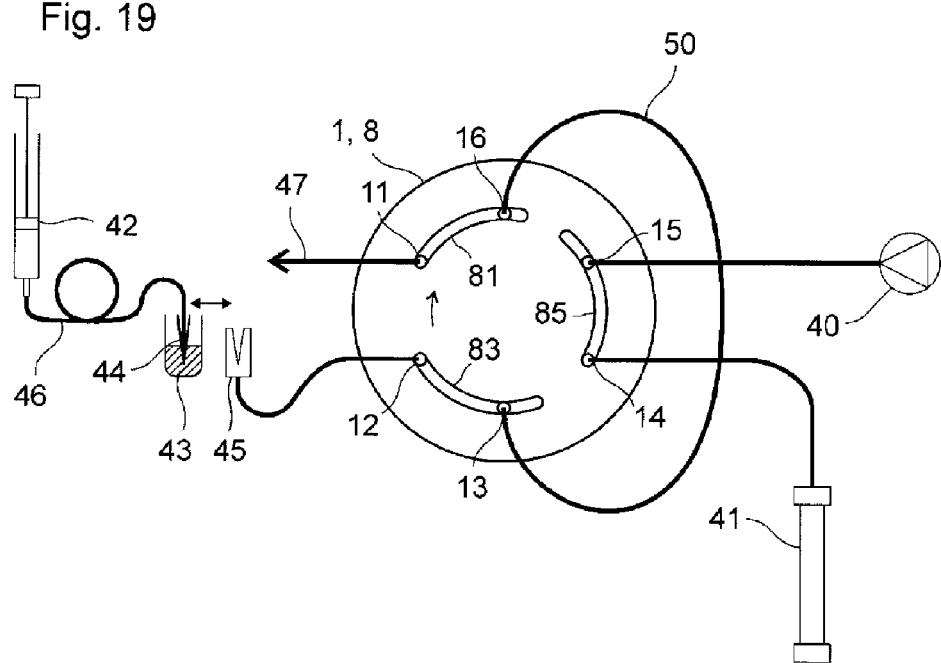
FIG. 19 shows a representation of a second embodiment of an autosampler according to the invention in the LOAD position, which likewise comprises the high-pressure injection valve of the embodiment according to FIGS. 12-18, in which however the connected fluidic components realize the "pushed loop" injection principle.

FIG. 19 shows the application of the invention to the known "pushed loop" principle. The LOAD position is shown. Syringe 42 here is connected directly to the sample needle 44 via a buffer capillary 46. The sample liquid 43 can now be drawn into buffer capillary 46. Then sample needle 44 can be moved into a needle seat 45 that is connected to port 12. This is indicated in FIG. 19 by an arrow. Sample liquid can now be pressed with syringe 42 into sample loop 50. A waste capillary 47, via which the displaced liquid is disposed of, is connected to port 11.

The "pushed loop" principle differs from the previously described "pulled loop" principle in the type of low-pressure side filling of sample loop 50. Therefore, all discussions with regard to the invention apply in the same manner as described above. However, the decompression of sample loop 50 now takes place via needle seat 45, which is connected to port 12. This is undesirable because sample liquid can escape at the needle seat, which leads to contamination of the next sample in the next filling of the sample loop.

Figure 20:
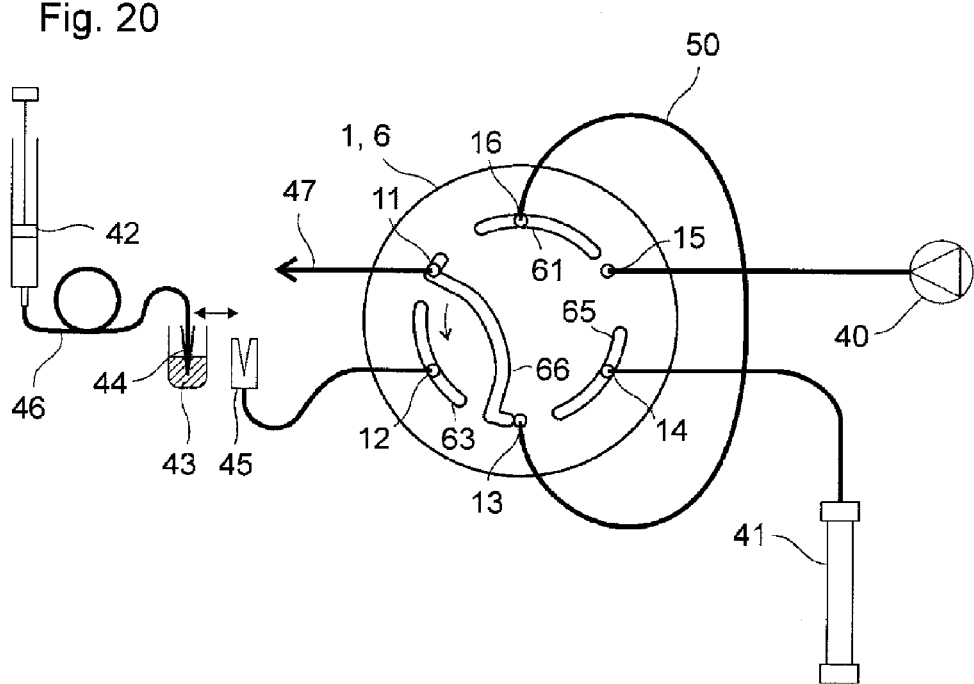
FIG. 20 shows a representation of a third embodiment of the autosampler according to the invention that comprises a second embodiment according to the invention of a high-pressure injection valve that is improved in relation to the realization of the "pushed loop" injection principle, wherein the high-pressure injection valve is situated in a position shortly before a decompression of the sample loop takes place.

FIG. 20 shows an improved embodiment of a high-pressure injection valve for the "pushed loop" principle. The arrangement largely corresponds to FIG. 19; however, an additional groove 66 that allows a decompression of sample loop 50 without liquid appearing at needle seat 45 is provided in modified rotor 6 alongside grooves 61, 63, 65 (which correspond to grooves 81, 83, 85). The critical point in time at which the decompression of the sample loop begins during the changeover from the INJECT position into the LOAD position is shown in FIG. 20. Groove 66 is already connected via port 11 to waste capillary 47 and is just reaching port 13. The pressure in the sample loop can then be reduced via groove 66, with the direction of flow again corresponding to the non-harmful situation demonstrated in FIG. 10. By means of the groove 66 according to the invention, the pressure in sample loop 50 can be successfully reduced without damage occurring to the rotor or stator and without liquid escaping at needle seat 45 during a decompression of the sample loop.

Figure 21:
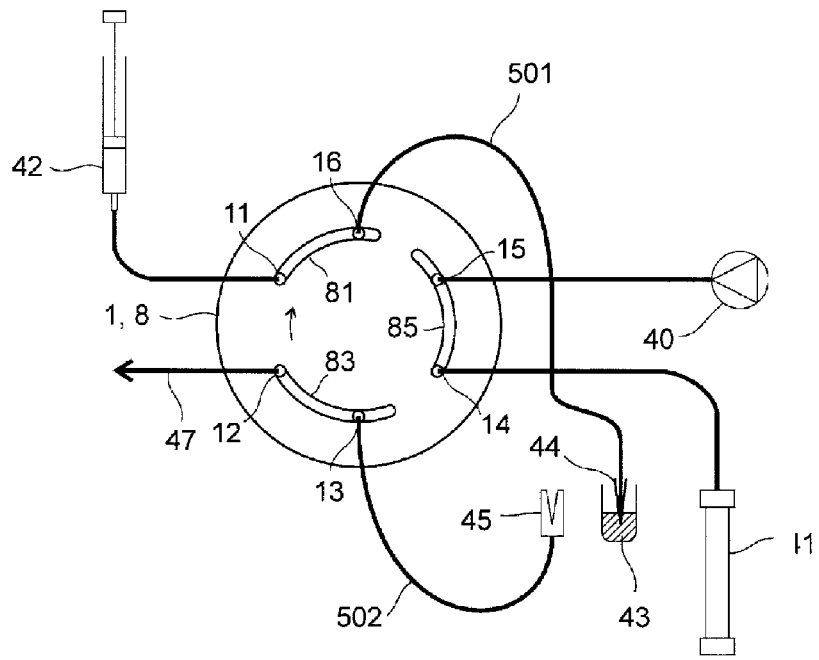
FIG. 21 shows a simplified schematic representation of a fourth embodiment of an autosampler according to the invention in the LOAD position with a high-pressure injection 19 valve as in FIG. 11 that is shown in section in the area of the contact plane of the rotor and the stator, with connected components, wherein the fluidic components are connected to realize the "split loop" injection principle.

FIG. 21 shows the application of the invention to the known "split loop" principle. Here the sample loop consists of two parts 501, 502. The upper part 501 is connected to sample needle 44 and the lower part 502 is connected to a needle seat 45. For taking a sample, the sample needle is placed in sample container 43. Sample liquid can now be drawn via the syringe 42 connected to port 11 into the upper part 501 of the sample loop. Subsequently the sample needle is moved into needle seat 45 so that the sample loop 501, 502 is thereby sealed tightly against high pressure. In the "split loop" principle as well, the differences are limited to the type of low-pressure side filling of the sample loop. After the closing of the sample loop, exactly the same pressure and flow conditions again result as were described above. Therefore, here as well, the mode of action of the invention does not differ from the discussions above.

As already explained, a fixation of the switching direction of the valve in relation to the connection sequence of the components is necessary for the realization of the invention. The decisive aspect is that in the switching from LOAD to INJECT the rotor is moved from the pump connector port 15 in the direction towards the column connector port 14, and in the reverse direction when switching back.

The actually required rotational direction thus depends on the connection sequence of pump and column. To simplify the description, an arbitrarily established connection sequence and the associated rotational direction were used. If the connection sequence is selected in reverse in the practical implementation of the invention, the rotation directions must be correspondingly adapted.

The invention can also be used in the same manner if a valve with more than six ports is used for the injection. For example, an autosampler is described in WO 2007062642 that can simultaneously perform a sample fractionation and operate with an 8-port injection valve. The two additional ports are used here to distribute already separated sample components exiting at the output of a chromatography column into different sample containers. These two ports are located between the connectors for the syringe and the sample needle, and are operated exclusively with low pressure so that no significant pressure differences can occur there. Therefore no measures for avoiding damage are required in this case. With regard to the other ports and the associated grooves, the invention can be applied in the same manner as described above.

In the injection valve according to the invention, all three grooves 81, 83, 85 are lengthened in comparison with prior art. The lengthening of groove 81 serves only to prevent damage to groove 85 from the hydraulic energy stored in column 41. Since the column and its feed line are constructed for chromatographic reasons with very little dead volume, this energy is generally so slight that no significant material damage arises even without the lengthening of groove 81.

Therefore a lengthening of groove 81 can be dispensed within the practical configuration of the first embodiment, i.e., only grooves 83 and 85 are lengthened in comparison with prior art, while groove 81 can have the same length as groove 21. This has the advantage that the distance between the ends of groove 85 and groove 81 need not be further reduced than is already the case due to groove 85, which has been lengthened in comparison with prior art. One can therefore prevent an excessively small distance between the groove ends from leading to sealing problems.

The decisive aspect for the functioning of the invention is that the switching processes take place in the proper temporal sequence. This is achieved by, among other things, the above-described lengthening of the grooves in the rotor. Since the rotor can be machined relatively easily (even retroactively), this is the preferred embodiment of the invention.

The necessary fixation of the switching sequence can also be achieved in an additional embodiment by modification of the stator, with an unchanged rotor.

Figure 1:
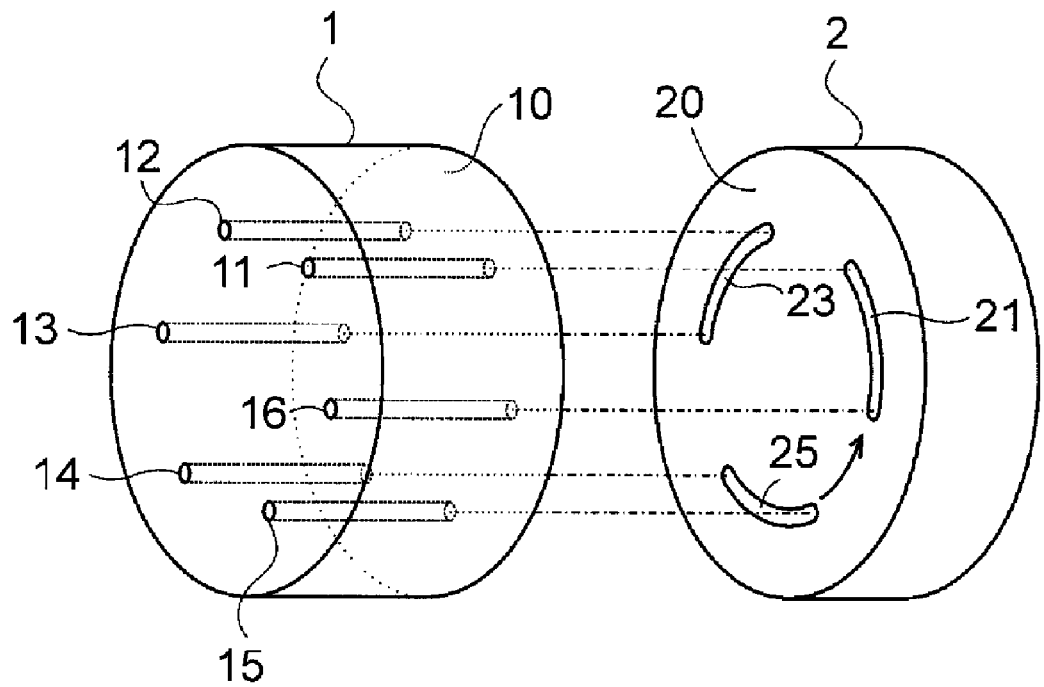
FIG. 1 shows a high-pressure injection valve according to prior art in a first switching position in a schematic perspective exploded view.
Figure 22:
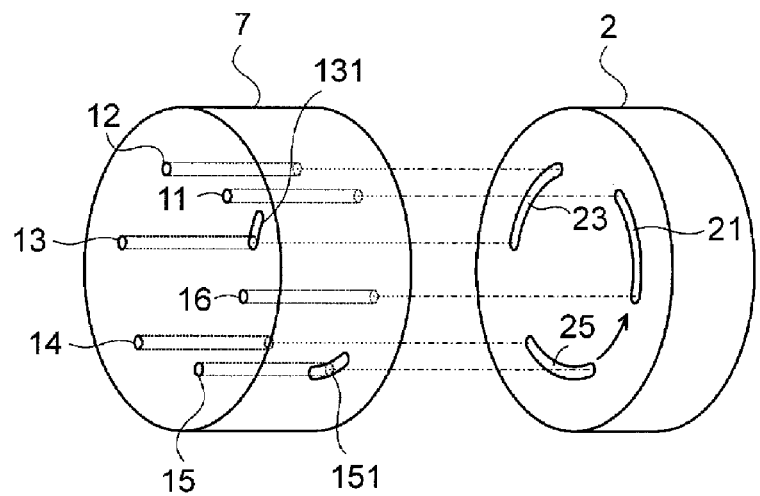
FIG. 22 shows a second embodiment of a high-pressure injection valve according to the invention in the operation-ready assembled state, in a schematic perspective exploded view.

In the same representation as in FIG. 1, FIG. 22 shows an injection valve according to the second embodiment of the invention with grooves 131, 151 machined into the modified stator 7. Rotor 2 is unchanged with respect to FIG. 1, with grooves 21, 23, 25. Groove 131 runs from port 13 in the direction of port 12 and has the effect that groove 23 is connected somewhat prematurely to port 13 when the valve is switched from the INJECT position into the LOAD position. Therefore the effect is exactly the same as shown in FIG. 16. Groove 151 runs from 11 port 15 in both directions. Groove 25 is thereby connected somewhat prematurely to port 15 in the switch from LOAD to INJECT, on the other hand, from INJECT to LOAD; groove 21 is connected prematurely to port 15.

Figure 23:
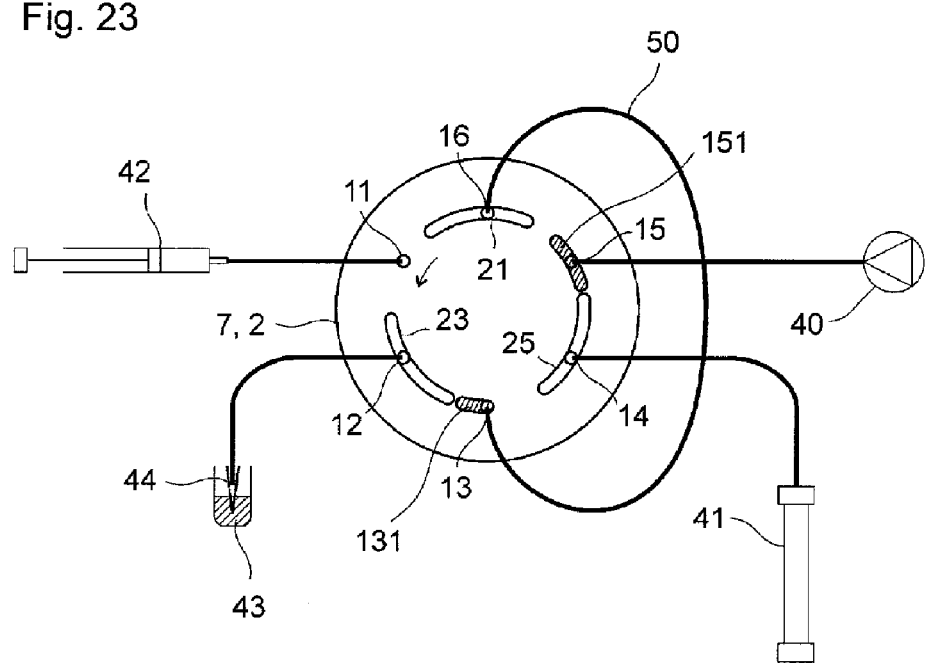
FIG. 23 shows a simplified schematic representation of an additional embodiment of an autosampler according to the invention with a high-pressure injection valve as in FIG. 22 that is shown in section in the area of the contact plane of the rotor and the stator and that is situated in a critical phase of the switching from INJECT to LOAD.

FIG. 23 shows the second embodiment of the invention in the same representation and the same switching position as FIG. 16. Grooves 131, 151 in the stator are shown hatched for better distinction. One recognizes that, just as in FIG. 16, groove 23 is connected somewhat prematurely to stator groove 131 and thus to port 13, and groove 25 is connected to stator groove 151 and thus to port 15. In the switch back, groove 21 is prematurely connected to the other end of stator groove 151 and thus to port 15. Since the flow is directed into the grooves of the rotor here as well, no damage occurs.

Thus, the effect of grooves 131, 151 in stator 7 is identical to the already described effect of the lengthened grooves 81, 83, 85 in rotor 8. This embodiment of the invention likewise prevents the damage observed in the prior art.

As can be seen in FIG. 6, the most serious damage 201 arises in the prior art at the end of groove 23. Therefore a substantial improvement of the valve's service life can be achieved if the damage is simply prevented from arising at this point. This can be achieved according to the first embodiment of the invention by undertaking the connection of the valve as in FIG. 12 and using only a single lengthened groove 83, while grooves 81 and 85 have the same length as grooves 21 and 25 in valves according to the prior art.

Corresponding to the previously described embodiment, the damage 201 can be avoided 11 merely by omitting groove 151 in FIG. 23.

Figure 24:
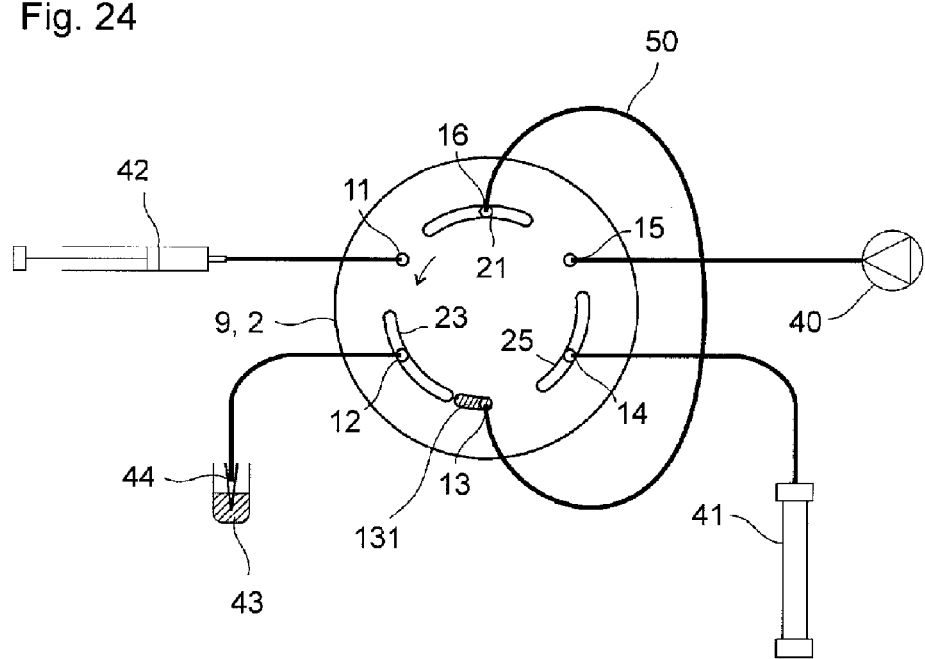
FIG. 24 shows a simplified schematic representation of an additional embodiment of an autosampler according to the invention with an additional embodiment according to the invention of a high-pressure injection valve that is shown in section in the area of the contact plane of the rotor and the stator and that is situated in a critical phase of the switching from INJECT to LOAD.

This yields an additional embodiment, which is illustrated in FIG. 24. Here stator 9 contains only a single groove 131 that, originating from port 13, runs the direction of port 12. FIG. 24 again shows the critical situation during the switching from INJECT to LOAD, when the pressurized sample loop 50 is just being connected to sample below 44. Pressure reduction takes place from stator groove 131 in the direction towards rotor groove 23, so that no damage appears.

This embodiment has the particular advantage that it can be realized with a "make-before-break" functionality by proper connection of an available finished valve, since only a single groove in the stator is required. The port furnished with a stator groove is not connected to the pump or column as actually foreseen however, but to the sample needle, so that the structure illustrated in FIG. 24 results. By means of this connection, the improvement of service life is achieved according to the invention in place of the actually envisioned "make-before-break" functionality.

It goes without saying that this embodiment can also be applied to other injection principles in the same manner as the previously described embodiments.

In conclusion it may be pointed out that the individual embodiments and refinements of the invention can be used both individually and in combination.

As used herein, the terms "comprising," "including," "having," "is provided," and the like are to be understood to be open-ended, that is, to mean including but not limited to.

The above described preferred embodiments are intended to illustrate the principles of the invention, but not to limit the scope of the invention. Various other embodiments and modifications to these preferred embodiments may be made by those skilled in the art without departing from the scope of the present invention.

The invention claimed is:

1. An autosampler for high-performance liquid chromatography, the autosampler comprising:
   (a) a high-pressure injection valve having at least six ports including first and second load ports for supplying or removing fluid under low pressure, first and second sample loop ports, and first and second high-pressure ports for supplying or removing fluid under high pressure;
      (i) wherein the ports are formed by channels in a stator of the high-pressure injection valve that are connected or are adapted to be connected at one end to a fluid line via a respective pressure-tight connector, and which have a predetermined port opening cross section at an end face of the stator;
- (ii) wherein a rotor of the high-pressure injection valve has an end face cooperating with the end face of the stator, in which rotor at least three grooves are formed that connect the predetermined port opening cross sections pressure-tightly, depending on the rotational position of the rotor with respect to the stator;
- (iii) wherein the at least three grooves run circumferentially and concentrically to the axis of rotation at least in such angle ranges in which a fluid flow is made possible between grooves and the corresponding ports;

(b) a sample loop that is connected at one end to one of the sample loop ports and at the other end to the other of the sample loop ports;

(c) a high-pressure pump that is connected to one of the high-pressure ports;

(d) wherein the at least three grooves of the rotor and the port opening cross sections are constructed and arranged such that:
- (i) in a LOAD position of the rotor the two high-pressure ports are connected to one another, and one of the sample loop ports is connected to one of the load ports and the respective other sample loop port is connected to the respective other load port;
- (ii) in an INJECT position of the rotor the two load ports are connected to one another and one of the high-pressure ports is connected to one of the sample loop ports and the other high-pressure port is connected to the other sample loop port, and
- (iii) both in the LOAD position and in the INJECT position, a first groove (load port groove) is connected to a load port, a second groove (sample loop port groove) is connected to a sample loop port, and a third groove (high-pressure port groove) is connected to a high-pressure port;

(e) wherein the rotor is forced against the stator by a pressure force that is high enough in order to effect a sealing of the grooves in the rotor surface for pressure fluids higher than 600 bar; and (f) wherein the at least three grooves or the port opening cross sections are provided and constructed in such a manner, and the rotational direction is selected in such a manner that, in a rotation of the rotor from the INJECT position into the LOAD position, the sample loop under high pressure is decompressed in such a manner
that the grooves or the port opening cross sections are constructed and arranged such that the connection between a selected one of the sample loop ports and a selected one of the load ports due to the movement of the load port groove in the direction towards the respective sample loop port is produced and maintained before the connection between the other sample loop port and the other load port that results due to the movement of the respective sample loop port in the direction of the respective load port is produced and maintained, for decompressing the sample loop.

2. The autosampler of claim 1, wherein the load port groove, the sample loop port groove and the high-pressure port groove are each constructed running in a circumferential direction and concentrically, and are permanently connected to their respective port in a transition from the LOAD position into the INJECT position and vice versa.

3. The autosampler of claim 1, wherein the port opening cross sections are provided in equidistant angular distances along a circle defined by the three grooves.

4. The autosampler of claim 1, wherein, in relation to switching from the INJECT position to the LOAD position, the load port groove is constructed to lead with respect to the sample loop port groove.

5. The autosampler of claim 1, wherein the port opening cross section of a respective load port that is not permanently connected to a respective groove extends in a groove shape in the direction towards the load port groove, the length of the groove-shaped extension of the port opening cross section being selected such that, in the changeover from the INJECT position to the LOAD position, an advancement function for decompressing the sample loop is realized.

6. The autosampler of claim 5, wherein the high-pressure port groove is constructed sufficiently long that the two high-pressure ports are connected in an angular position in which the decompression of the sample loop takes place, or over the entire angle range of the rotational movement in which the decompression of sample loop takes place.

7. The autosampler of claim 5, wherein the port opening cross section of the high-pressure port that is not permanently connected to a groove during the switching process is extended in a groove shape in the direction towards the high-pressure port groove, the length of the groove-shaped extension of the port opening cross section being selected such that the two high-pressure ports are connected during the changeover from the INJECT position to the LOAD position in the rotational position in which the decompression of sample loop takes place, or over the entire angle range of the rotational movement in which the decompression of sample loop takes place.

8. The autosampler of claim 5, wherein the rotational direction is selected such that, and grooves or the port opening cross sections are constructed and arranged such that, in a rotation of the rotor from the LOAD position into the INJECT position, the substantially pressure-free sample loop is subjected to high pressure in a manner such that:
the connection between the sample loop port that is permanently connected to a groove during the switching movement and the respective high-pressure port is first produced and maintained, the sample loop port groove being moved for this purpose in the direction towards the respective high-pressure port; and
following that, the connection between the other high-pressure port and the other sample loop port is produced and maintained, the high-pressure port groove being moved in the direction towards the respective sample loop port.

9. The autosampler of claim 8, wherein the sample loop port groove that is moved towards an adjacent high-pressure port during the changeover from the LOAD position to the INJECT position is constructed to lead with respect to the high-pressure port groove.

10. The autosampler of claim 8, wherein the port opening cross section of the high-pressure port that is not permanently connected to a groove during the switching process is extended in a groove shape in the direction towards the load port groove, the length of the groove-shaped extension of the port opening cross section being selected such that, in the changeover from the LOAD position to the INJECT position, the advancement function for pressurizing the sample loop is realized.

11. The autosampler of claim 1, further comprising a control unit and a controllable drive unit for the rotational movement of the rotor.

12. The autosampler of claim 11, wherein the control unit is configured to control the drive unit such that decompression of the sample loop in the changeover from the INJECT position into the LOAD position takes place essentially completely via a desired one of the sample loop ports.

13. The autosampler of claim 12, wherein the control unit is configured to influence the speed of the rotational movement such that the time span over which a decompression of sample loop can take place via the desired sample loop port is sufficient to guarantee an essentially complete decompression.

14. The autosampler of claim 13, wherein the control unit is configured to slow the rotary movement over the angle range in which a decompression is possible, or is configured to stop the rotary motion in this angle range for a predetermined time span.

15. The autosampler of claim 11, wherein the control unit is configured to control the drive unit such that the pressurization of the sample loop in the changeover from the LOAD position into the INJECT position takes place essentially completely via a desired one of the sample loop ports.

16. The autosampler of claim 15, wherein the control unit is configured to influence the speed of the rotational movement such that the time span over which a pressurization of the sample loop can take place via the desired sample loop port is sufficient to guarantee an essentially complete pressurization.

17. The autosampler of claim 16, wherein the control unit can is configured to slow the rotary movement over the angle range in which a pressurization is possible, or is configured to stop the rotary motion in this angle range for a predetermined time span.

18. An autosampler for high-performance liquid chromatography, the autosampler comprising:
   (a) a high-pressure injection valve having at least six ports including first and second load ports for supplying or removing fluid under low pressure, first and second sample loop ports, and first and second high-pressure ports for supplying or removing fluid under high pressure;
      (i) wherein the ports are formed by channels in a stator of the high-pressure injection valve that are connected or are adapted to be connected at one end to a fluid line via a respective pressure-tight connector, and which have a predetermined port opening cross section at an end face of the stator;
      (ii) wherein a rotor of the high-pressure injection valve has an end face cooperating with the end face of the stator, in which rotor at least three grooves are formed that connect the predetermined port opening cross sections pressure-tightly, depending on the rotational position of the rotor with respect to the stator;
      (iii) wherein the at least three grooves run circumferentially and concentrically to the axis of rotation at least in such angle ranges in which a fluid flow is made possible between grooves and the corresponding ports;
   (b) a sample loop that is connected at one end to one of the sample loop ports and at the other end to the other of the sample loop ports;
   (c) a high-pressure pump that is connected to one of the high-pressure ports;
   (d) wherein the at least three grooves of the rotor and the port opening cross sections are constructed and arranged such that:
      (i) in a LOAD position of the rotor the two high-pressure ports are connected to one another, and one of the sample loop ports is connected to one of the load ports and the respective other sample loop port is connected to the respective other load port;
      (ii) in an INJECT position of the rotor the two load ports are connected to one another and one of the high-pressure ports is connected to one of the sample loop ports and the other high-pressure port is connected to the other sample loop port, and
      (iii) both in the LOAD position and in the INJECT position, a first groove (load port groove) is connected to a load port, a second groove (sample loop port groove) is connected to a sample loop port, and a third groove (high-pressure port groove) is connected to a high-pressure port;
   (e) wherein the rotor is forced against the stator by a pressure force that is high enough in order to effect a sealing of the grooves in the rotor surface for pressure fluids higher than 600 bar; and
   (f) wherein the at least three grooves or the port opening cross sections are provided and constructed in such a manner, and the rotational direction is selected in such a manner that, in a rotation of the rotor from the INJECT position into the LOAD position, the sample loop under high pressure is decompressed in such a manner that an additional tension-relieving groove is provided in the rotor that is constructed such that before reaching the LOAD position, in a defined rotational position or over a defined angular range, a connection is produced and maintained between a selected one of the sample loop ports and a selected one of the load ports that are not permanently connected to a groove, wherein the end of tension-relieving groove that is connected to a selected sample loop port or the port opening cross sections runs concentrically and in the circumferential direction over a sufficiently long tension-relieving region, which is dimensioned such that the flow speeds of the fluid flow that results at the achievement of the overlapping of a tension-relieving groove and the port opening cross section are reduced sufficiently that damage to the stator or the rotor is avoided.

19. The autosampler of claim 18, further comprising a control unit and a controllable drive unit for the rotational movement of rotor.

20. The autosampler of claim 19, wherein the control unit is configured to control the drive unit such that decompression of the sample loop in the changeover from the INJECT position into the LOAD position takes place essentially completely via a desired one of the sample loop ports.

* * * * *

UNITED STATES PATENT AND TRADEMARK OFFICE
CERTIFICATE OF CORRECTION

| | | |
|---|---|---|
| PATENT NO. | : 8,196,456 B2 | Page 1 of 1 |
| APPLICATION NO. | : 12/331228 | |
| DATED | : June 12, 2012 | |
| INVENTOR(S) | : Hermann Hochgraeber and Gervin Ruegenberg | |

It is certified that error appears in the above-identified patent and that said Letters Patent is hereby corrected as shown below:

At column 5, line 44: change "before the 11 LOAD" to read --before the LOAD--.

At column 11, line 29: change "injection 19" to read --injection--.

At column 14, line 17: change "applied 11 accordingly" to read --applied accordingly--.

At column 15, line 66: change "from 11 port 15" to read --from port 15--.

At column 16, line 25: change "be avoided 11 merely" to read --be avoided merely--.

At column 19, line 24: change "can is configured" to read --is configured--.

Signed and Sealed this
Twenty-fourth Day of July, 2012

David J. Kappos
*Director of the United States Patent and Trademark Office*